United States Patent [19]

Marshall et al.

[11] Patent Number: 5,631,159
[45] Date of Patent: May 20, 1997

[54] LIPID-MODIFIED SERUM FREE MEDIA

[75] Inventors: Paul G. Marshall, Berkley; Patrick M. Guertin, Mendon, both of Mass.

[73] Assignee: Creative BioMolecules, Inc., Hopkinton, Mass.

[21] Appl. No.: 124,676

[22] Filed: Sep. 22, 1993

[51] Int. Cl.$^6$ .................................................. C12N 5/00
[52] U.S. Cl. .......................... 435/383; 435/395; 435/404
[58] Field of Search ............................. 435/240.3, 240.31

[56] References Cited

U.S. PATENT DOCUMENTS

| | | | |
|---|---|---|---|
| 4,968,590 | 11/1990 | Kuberasampath et al. | 530/326 |
| 5,011,691 | 4/1991 | Oppermann et al. | 424/423 |
| 5,153,125 | 10/1992 | Kobayashi | 435/128 |
| 5,250,421 | 10/1993 | Kaufman et al. | 435/69.6 |

FOREIGN PATENT DOCUMENTS

| | | |
|---|---|---|
| 90/03430 | 4/1990 | WIPO. |
| WO90/07007 | 6/1990 | WIPO. |
| 91/05802 | 5/1991 | WIPO. |

OTHER PUBLICATIONS

Bashir et al., "Phospholipids Regulate Growth and Function of MDCK Cells in Hormonally Defined Serum Free Medium," *In Vitro Cell. Dev. Biol.*, 28A:663–668 (1992).
Bettger et al., "The Critical Role of Lipids in Supporting Clonal Growth of Human Diploid Fibroblasts in a Defined Medium," *Growth of Cells in Hormonally Defined Media (Book A)*, vol. 9, Cold Spring Harbor, N.Y., Cold Spring Harbor Labatory, pp. 61–64 (1982).
Bromke, "A Serum–free, Lipid–Supplemented Medium for the Growth of Trichomonas Vaginalis," *J. Microbiological Methods*, 6:55–59 (1986).
Goodwin, "Lipid Cell Culture Supplements," *Nature*, 347:209–210 (1990).
Hewlett, "Strategies for Optimising Serum–free Media," *Cytotechnology*, 5:3–14 (1991).
Hysmith et al., "Degradation of Human Myelin Phospholipids by Phospholipase–Enriched Culture Media of Pathogenic Naegleria Fowleri," *Biochimica et Biophysica Acta*, 712:698–701 (1982).
Hysmith et al., "Elevated Levels of Cellular and Extracellular Phospholipases From Pathogenic Naegleria Fowleri," *Biochimica et Biophysica Acta*, 711:26–32 (1982).
Imagawa et al., "Phospholipids Containing Polyunsaturated Fatty Acyl Groups are Mitogenic for Normal Mouse Mammary Epithelial Cells in Serum–free Primary Cell Culture," *Proc. Natl. Acad. Sci.*, 86:4122–4126 (1989).
Maiorella et al., "Supply of Lipids in Animal Cell Culture Media," *Abstr. Pap. Am. Chem. Soc.*, No. 143 (1988).
Kovar, "Hybridoma Cultivation in Defined Serum–free Media: Growth–supporting Substances," *Folia Biologica*, 33:377–384 (1987).
Maurer, "Towards Serum–free, Chemically Defined Media for Mammalian Cell Culture," *Animal Cell Culture: A Practical Approach*, 2nd Ed., R.I. Freshney, Ed., Oxford University Press, pp. 15–46 (1992).

Minor et al., "Lysomal Hydrolysis of Lipids in a Cell Culture Model of Smooth Muscle Foam Cells," *Experimental and Molecular Pathology*, 54:159–171 (1991).
Miyazaki et al., "Extending Effects of Phospholipids, Cholesterol, and Ethanolamines on Survival of Adult Rat Hepatocytes in Serum–free Primary Culture," *Res. Exp. Med.*, 191:77–83 (1991).
Mizrahi et al., "Media for Cultivation of Animal Cells: An Overview," *Cytotechnology*, 1:199–214 (1988).
Mochizuki et al., "Serum Proteins Neutralize the Toxic Effect of Lysophosphatidyl Choline," *Current Eye Research*, 2:621–624 (1982).
Takeda et al., "Role of Serum in Inhibition of Cultured Lymphocytes by Lysophosphatidylcholine," *Biochimica et Biophysica Acta*, 710:87–98 (1982).
Uthe et al., "Phospholipase A$_2$: Action of Purified Phospholipids as Affected by Deoxycholate and Divalent Cations," *Can. J. Biochem.*, 49:776 (1971).
Valette et al., "Effects of Alkyl Lysophospholipids on Breast Adenocarcinomas MCF–7 Cells in a Serum–Free Medium," *Proc. of the American Assoc. for Cancer Research*, 32:431 (1991).
van Corven et al., "Lysophosphatidate–Induced Cell Proliferation: Identification and Dissection of Signaling Pathways Mediated by G Proteins," *Cell*, 59:49–54 (1989).
Facci et al., "Dissociation of the Stellate Morphology From Intracellular Cyclic AMP levels in Cultured Rat Brain Astroglial Cells: Effects of Ganglioside $G_{M1}$ and Lysophosphatidylserine", *J. of Neurochemistry*, 48, No. 2:566–573 (1987).
Homma et al., "Vitamin D–binding Protein (Group–Specific Component) is the Sole Serum Protein Required For Macrophage Activation After Treatment of Peritoneal Cells With Lysophosphatidycholine", *Immunology and Cell Biology*, 71:249–257 (1993).
"Preparation of Phospholipids and Lysophospholipids with Reduced Amount of Neutral Lipids", *Chemical Abstracts*, 109:436 (1988) (Abstract).
"Alkaline Hydrolysis of Phosphoglycerides on Thin Layer Plates in Situ", *9–Biochem. Methods*, 106:349 (1987) (Abstract).
"Hydrolysis of Diacylglycerophospholipids With Phospholipase A$_2$", *16–Fermentations*, 115:799 (1991).
Arakawa et al, "Neurite—Act. of Phosphotidylinostol & Other Lipids on Fetal Rat Septal . . . "1991, pp. 1864–1871.
Fujita et al., "Process for Purification of Glyceryl Phosphates" 1988, Japanese Abst.

*Primary Examiner*—John W. Rollins
*Assistant Examiner*—Deborah K. Ware
*Attorney, Agent, or Firm*—Testa, Hurwitz & Thibeault, LLP

[57] ABSTRACT

Methods are provided for producing serum-free, animal cell culture media which have enhanced cell culture properties, such as cell growth, cell viability and protein production properties. The cell culture properties of standard serum-free media formulations, which include compositions such as inorganic salts, glucose, fatty acids, amino acids and vitamins, can be enhanced according to the methods of the invention, by providing the media with an additive. The additive in one embodiment can be produced by the acid or base catalyzed hydrolysis of a phosphoglyceride.

27 Claims, 3 Drawing Sheets

LIPID-MODIFIED SERUM FREE MEDIA

FIELD OF INVENTION

The present invention relates generally to ex vivo cell cultivation, and more particularly, to cell culture media and methods for their production.

BACKGROUND OF THE INVENTION

When a cell is removed from its original tissue or organism and placed in culture, the medium must provide all the environmental conditions that the cell has been exposed to in vivo; only then will it be able to survive, to proliferate, and to differentiate or maintain its differentiated phenotype. Thus, extracellular medium must meet the essential requirements for survival and growth (i.e. must provide nutritional, hormonal, and stromal factors). Where cells are cultured as part of a system to produce biologicals, e.g., for the production of vaccines or recombinant protein, the culturing medium also should not interfere with the cell's production of the desired biological. Among the biological fluids that have proved successful for culturing cells outside the body, serum has gained the most widespread significance.

However, there are a number of disadvantages with serum-containing media, particularly as part of a recombinant biologicals production system, including difficulties with sterilization, inconsistent variation between serum batches, the presence of extraneous serum constituents including indefinable and potentially cytotoxic constituents from which the biological product of interest must be purified, and risk of contaminants. Accordingly, the art long has sought to create non-serum culture media (including "serum-free" and "chemically-defined" media) which provide the necessary environmental conditions for cell growth and viability. Defining components necessary for a non-serum culturing media has been an on-going effort in the art. In many non-serum culture media, cell growth often is slower, and cell density and saturation levels, as well as cell viability, may be diminished. In addition, media formulations found useful for cell growth often are not optimal for recombinant protein production, requiring a change in culture media when protein production is to be induced, or a compromise in desired protein production levels.

Mizrahi and Lazar (*Cytotechnology* (1988) 1:199–214) describes the general state of the art of serum-free, chemically defined media for ex vivo mammalian cell cultivation.

Along with an energy source, a nitrogen source, vitamins, inorganic salts, nucleic acid precursors, and oxygen, fats (lipids) and fat-soluble components are critical elements for non-serum containing culture medium. Among the lipids found to be useful in serum-free or chemically defined media are phospholipids commonly associated with the cell membrane, and various lipid and phospholipid precursors. Goodwin, et al (1990) *Nature* 347:209–210 describes lipid supplements useful in serum-free media. Bromke, et al (1986) *J. Microbiol. Methods*, 6:55–59 describe the use of cholestrol and oleic acid in serum-free media. Imagawa et al., (1989) PNAS 86:4122–4126 describe the use of the lipid precursors dilinoleoyl phosphatidic acid and phosphatidyl serine to stimulate growth of epithelial cells in a serum-free medium. Bashir et al. (1992) *In Vitro Cell Dev. Biol.* 28A:663–668 describes the use of the lipid precursors phosphatidic acid and lysophosphatidic acid to stimulate the growth of kidney cells in serum-free media.

International application PCT/US90/03430, published Apr. 15, 1990, discloses a serum-free cell culture medium for enhanced cell growth that includes the phospholipid precursors choline, ethanolamine, phosphatidyl choline and phosphatidyl ethanolamine. Miyazaki et al. (1991) *Res. Exp. Med.* 191:77–83 describe the use of phosphatidyl ethanolamine and phosphatidyl choline, as well as the phospholipid precursors ethanolamine and phosphoethanolamine, to prolong survival of rat hepatocytes in culture. Kovar (1987) *Folia Biologica* 33:377–384 describes the use of dipalmitoyl lecithin, cholesterol and linoleic acid to promote the growth of hybridomas in serum-free media.

It is an object of the invention to provide an improvement in serum-free cell culture media. Another object is to provide a cell culture media, and methods for its production, having improved cell cultivation properties, including enhanced cell growth and cell viability, and enhanced production of recombinant biologicals. Another object of this invention is to provide serum-free media having enhanced cell culture properties and which can be utilized in a wide range of cell culture systems for the recombinant production of biologicals, including proteins, using any of a number of cell lines and recombinant protein expression systems known in the art. Still another object of the invention is to provide a media formulation having particular utility for the recombinant production of bone morphogenic proteins. It is a further object of the invention to provide methods for consistently and reproducibly producing such serum-free media having improved cell cultivation properties.

These and other objects and features of the invention will be apparent from the description, figures, and claims which follow.

SUMMARY OF THE INVENTION

An improvement in serum-free (non-serum containing) cell culture media having enhanced cell cultivation properties, including enhanced cell growth, cell viability and recombinant biologicals production, now has been discovered. The serum-free media formulations of the invention have particular utility in animal cell culturing systems for the production of biologicals of interest, including recombinant proteins. As described herein, the serum-free media formulations of the invention include the elements provided in standard serum-free media formulations, including an energy source such as glucose, inorganic salts, fat soluble components, a nitrogen source and vitamins. In addition, and as disclosed herein, the serum-free media formulations of the invention also include an additive which unexpectedly has a synergistic effect, when combined with a standard formulation, to enhance significantly the overall cell culture properties of the medium.

As used herein "serum-free" means a culture medium formulated in the absence of serum, and includes both the media formulations defined in the art as "serum-frre" media (which may otherwise be protein supplemented), "protein-free" media, (no protein supplementation) and "chemically defined" (ultra-pure with or without small molecular constituents, genetically engineered peptides or proteins).

In one embodiment, to improve the cell culture properties of the media, the serum-free media are provided with an additive having the formula:

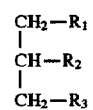

wherein one of $R_1$ or $R_2$ is OH, and another of $R_1$ and $R_2$ is OH or:

wherein $R_4$ is a $C_1-C_{26}$ hydrocarbon, preferably a $C_{10}-C_{24}$ fatty acid. Additionally, $R_3$ is

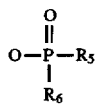

wherein one of $R_5$ and $R_6$ is $O^-$, and the other is an alcohol, and the phosphate is esterified to the hydroxyl group of the alcohol. Examples of common alcohol moieties for one of $R_5$ and $R_6$ include serine, ethanolamine, choline, inositol and other alcohols commonly associated with membrane phospholipids.

In another embodiment, the additive comprises a lysophosphatidyl ester formed as a degradation product of a membrane phosphoglyceride ester.

As used herein, "phosphoglyceride ester" is a substituted glycerol, wherein the hydroxyl groups at $C_1$ and $C_2$ each are esterified to the carboxyl group of a fatty acid, and the $C_3$ hydroxyl group is esterified to a phosphate ($PO_3^{2-}$).

Exemplary phosphoglyceride esters include phosphatidyl ethanolamine, phosphatidylcholine, phosphotidylserine and phosphatidylinositol and other phospholipids that comprise part of a cell membrane.

As used herein, a lysophosphatidyl ester is a phosphoglyceride ester hydrolyzed to release at least one of its two fatty acid chain components, (e.g., a $C_1-C_{26}$ hydrocarbon). Exemplary lysophosphatidyl esters useful as additives in the serum formulations of the invention include lysophatidyl ethanolamine, lysophosphatidyl choline, lysophophatidyl serine and other lysophosphatidyl ester hydrolysis products of phospholipids which comprise part of a cell membrane.

In another embodiment, the media formulations are made by adding to the media hydrolysis products of a phosphoglyceride ester composition. Exemplary phosphoglyceride ester compositions include compositions containing phosphoglyceride esters typically associated with a cell membrane, including, without limitation, phosphatidyl choline, phosphatidyl ethanolamine, phosphatidyl serine, and phosphatidyl inositol.

The additive may be formed, in one embodiment, by the hydrolysis of one or more commercially available phosphoglyceride esters, including commercially available phosphatidyl serine, phosphatidyl ethanolamine, phosphatidyl choline, or phosphatidyl inositol compositions. The phosphoglyceride esters may be hydrolyzed by an acid hydrolysis or by base saponification using standard methodologies well known in the art. The phosphoglyceride may be hydrolyzed in one embodiment by heating the phosphoglyceride ester in an acid or base solution to temperature greater than 40° C. In another preferred embodiment, the ester is heated to a temperature within the range of 45°–90° C., preferably 50°–70° C., for at least 15 minutes, preferably at least 20 minutes. The concentration of the acid or base in the solution may be adjusted to between about 0.05M to 10M of the acid or base. In another embodiment the phosphoglyceride ester is acid hydrolyzed in a solution having a pH in the range of about 0.2–4, preferably in the pH range of 0.2–2. In another embodiment, the phosphoglyceride ester is base saponified in a solution having a pH in the range of about 8–14, preferably in the pH range of 10–14. The acid hydrolysis can be conducted using acids such as hydrochloric acid, sulfuric acid, phosphoric acid or nitric acid, either in an aqueous solvent or in an organic solvent, such as ethanol. The base saponification of the phosphoglyceride ester may be conducted using a base such as sodium hydroxide, potassium hydroxide or ammonium hydroxide, which also may be water or alcohol-based.

When the hydrolysis products of a phospholipid composition are added to standard serum-free culture media, the resulting media demonstrate unexpected enhanced cell culture properties, including enhanced cell growth, cell viability and recombinant biologicals production, as compared with the media formulated without the additive. Inclusion of the additive has an unexpected synergistic effect, when combined with a standard formulation, to enhance the ex vivo culture properties of the cells.

In another embodiment of the invention, a preferred media formulation is a formulation that includes the hydrolysis products of one or more phospholipid compositions, and a full complement of amino acids.

In still another embodiment of the invention, a preferred media formulation is one that includes the hydrolysis products of one or more phospholipid compositions, and a phospholipid precursor.

The improved cell culture media are reproducible and easy to make, and consistently demonstrate enhanced cell growth and recombinant protein production properties. The improved media thus allow the artisan to use one media formulation for both cell culturing and recombinant biologicals production, including recombinant protein production, without a need to change formulations or otherwise compromise recombinant protein production yields.

The improved cell culture formulations of the invention have utility for both vertebrate and invertebrate cell culture systems, including, without limitation, human, bovine, equine, primate, and other mammalian cells, non-mammalian cells, such as xenopus cell systems, and drosophila, and other insect (invertebrate) cells, as well as biosynthetic hybrid cell lines, including, for example, hybridomas. The improved cell culture formulation also has utility for the production of a variety of biologicals, including natural-sourced molecules, vaccines and recombinant proteins, such as antibodies, growth factors, members of the blood cascade, cytokines and morphogenic proteins, including true bone morphogens such as those described in U.S. Pat. No. 5,011,691.

The cell culture media formulations of the invention have particular utility in the culturing of chinese hamster ovary (CHO) cell lines, for the recombinant productions of true tissue morphogens such as OP1 and other natural-sourced, recombinantly produced or biosynthetic tissue morphogens known in the art and described, for example, in U.S. Pat. No. 5,011,691.

The foregoing and other objects, features and advantages of the present invention will be made more apparent from the following detailed description of the invention.

BRIEF DESCRIPTION OF THE FIGURES

The foregoing and other objects and features of this invention, as well as the invention itself, may be more fully understood from the following description, when read together with the accompanying drawings, in which.

DETAILED DESCRIPTION

Figure 1:
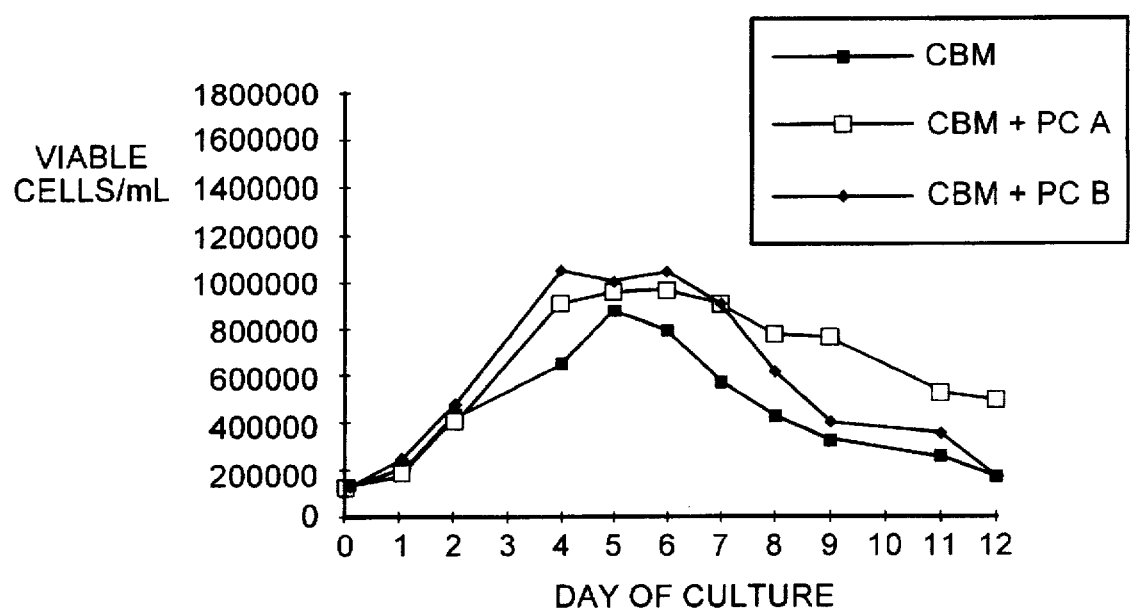
FIG. 1 is a graph of viable cell density versus day of culture for CHO-1 cells.

The invention provides an improvement in serum-free cell culture media having enhanced cell growth, cell viability and/or biologicals production properties. The improved media comprise a membrane lipid phosphoglyceride ester degradation product. To date, the art has sought to add lipids and lipid precursors to enhance the cell cultivation properties of serum-free medium. It now has surprisingly been discovered that phospholipid degradation products have unexpected synergistic effects, when combined with standard formulation, to produce media with enhanced cell culture properties. The additive is prepared easily as described herein and can be used in a range of media for a variety of cells and cell culture systems.

Presented below is a detailed description of the improvement in the cell culture media, and methods for their production, as well as general considerations for culture media formulation in which the additive is useful, detailed descriptions on how to make and use the additive and cell culture media of the invention, and several non-limiting examples demonstrating the utility of the improved media for enhancing cell growth, cell viability and recombinant protein production of cultured cells.

A. Serum-Free Cell Culture Media Additive and Methods for its Production.

In one embodiment, a serum-free medium having improved cell cultivation properties is provided by including in the medium an additive having the formula:

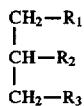

wherein one of $R_1$ or $R_2$ is OH, and another of $R_1$ or $R_2$ is OH or:

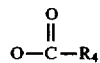

wherein $R_4$ is a $C_1$–$C_{26}$ hydrocarbon. The hydrocarbon preferably is long chain ($C_{10}$–$C_{24}$) fatty acid having a structure found in membrane lipids. Exemplary fatty acids found in cell membranes include saturated fatty acids such as lauric acid ($C_{12}$), myristic acid ($C_{14}$), palmitic acid ($C_{16}$), steric acid ($C_{18}$), arachidic acid ($C_{20}$), lignoceric acid ($C_{24}$), and unsaturated fatty acids such as palmitoleic acid ($C_{16}$), oleic acid ($C_{18}$), linoleic acid ($C_{18}$), linolenic acid ($C_{18}$), and arachidonic acid ($C_{20}$). Additionally, in the additive, $R_3$ is

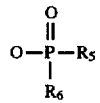

wherein one of $R_5$ and $R_6$ is $O^-$, and the other is an alcohol esterified to the phosphate group through its hydroxyl moiety. In a preferred embodiment, one of $R_5$ and $R_6$ is an alcohol normally associated with membrane phospholipids. Exemplary alcohols include serine, ethanolamine, choline and inositol. The additives of this formula are referred to herein as lysophosphoglyceride esters.

In another embodiment, the additive comprises one or more hydrolysis products of a phospholipid ester, preferably a phospholipid ester that normally is associated with a cell membrane including, for example, phosphatidyl choline (PC), phosphatidyl ethanolamine (PEA), phosphatidyl insitol (PI), phosphatidyl serine (PS) and the like.

The additive may be formed in one embodiment by the acid hydrolysis or base saponification of a phosphoglyceride ester as described in detail below. Alternatively, the additive may be formed by enzymatic hydrolysis of a phosphoglyceride ester, e.g., using a phospholipase available in the art such as phospolipase $A_2$, a phospholipase which selectively hydrolyzes the 2-acyl bond of 3-n-phosphoglycerides. Uthe et al., Can. J. Biochem., 49:776 (1971).

A.1. Acid Hydrolysis

Phosphoglyceride esters can be acid hydrolyzed using standard methodologies well known in the art to produce additives useful in the media formulations of the invention. Currently preferred is to hydrolyze the phosphoglyceride ester by heating it in an acid solution to a temperature of at least about 40° C., preferably in the range of about 45°–90° C., most preferably 50°–70° C., for at least 10 minutes, preferably at least 20 minutes. Heating the solution for longer than 90 minutes does not appear to provide additional efficacy. As will be appreciated by those having ordinary skill in the art, hydrolysis also will occur at room temperature, but this requires an extended period of time (e.g., at least several days, sometimes greater than 7–14 days, and complete hydrolysis can not be guaranteed by this means). The currently most preferred methodology is to heat the solution for between about 30–50 minutes at a temperature within the range of about 60°–65° C. The acidic solution may be created by exposing the phosphoglyceride ester to a solution having a pH within the range of about 0.2–4, preferably in the range of 0.2–2. In one embodiment the acidic solution is made by adding an acid to a final concentration of between about 0.5M to 10M of the acid in the solution. Acids such as hydrochloric acid, sulfuric acid, phosphoric acid or nitric acid may be utilized to advantage. The hydrolysis may be conducted in aqueous solvents, or in an alcohol such as ethanol. For example, a medium having enhanced cell culture properties can be prepared in one embodiment by adding phosphatidyl choline to a volume of 200 proof ethanol and about a 1:10 volume of 1N (1M) HCl. The solution then may be heated on a water bath for 30 to 45 minutes at 60° C. to 65° C. Subsequently, an approximately 1:1000 volume of the hydrolyzed phosphatidyl choline solution per liter of medium is added directly to the serum-free medium, to produce a medium having improved cell culture properties.

A.2. Base Saponification.

The phosphoglyceride ester also may be hydrolyzed by base saponification, e.g., by heating the phosphoglyceride ester in a basic solution at a temperature greater than 40° C. for at least about 10 minutes, preferably at least 20 minutes. Heating the solution for more than 90 minutes does not appear to provide additional efficacy. Currently preferred is heating to a temperature within the range of 50°–70° C. for 30–50 minutes. The basic solution may be created by exposing the phosphatidyl ester to a solution having a pH within the range of about 8–14, preferably 10–14. In one embodiment, the basic solution may be formulated by adjusting the solution to a concentration of 0.05M to 10.0M of a base such as sodium hydroxide, potassium hydroxide or ammonium hydroxide.

The hydrolyzed phospholipid then can be added to the medium as is, and the mixture sterilized as described below.

B. Cell Culture Media-General Considerations

The cell culture properties of a wide range of serum-free media formulations known in the art may be improved by addition of the additive disclosed herein. As will be appreciated by those having ordinary skill in the art, many individualized media formulations have been developed over the years to maximize cell growth, cell viability and/or biologicals production for a given cultured cell or cell line. These media compositions differ from one another, for example, in the number, type and concentration of growth factors, antibiotics and amino acid complements added to the media, and may also include components such as protease inhibitors, and one or more anti-foaming agents, particularly where cells are grown in suspension. Other individualized components include additives that enhance recombinant protein production. For example, where the host cell was developed for gene amplification of a recombinant protein, the selectable marker DHFR (dihydrofolate reductase) typically comprises part of the transfected host cell as a selectable marker, and methotrexate is included in the culture medium. Insulin or other growth factors such as IGF that play a role in the energy source cascade also often are included to enhance cell growth.

The additive disclosed herein is anticipated to have a synergistic effect on individualized media formulations as well as in standard formulations.

All serum-free media formulations include essential components which permit cell growth, including (1) an energy source, typically glucose or glutamine, or other sugars such as fructose, galactose, mannose, and the like; (2) a nitrogen source, typically obtained via inclusion of one or more amino acids; and (3) vitamins, which are cofactors in enzyme reactions. Also essential are a wide range of inorganic salts, including $Na^+$, $K^+$, $Ca^{2+}$, $Mg^{2+}$, $Cl^-$, $HPO_3^{2-}$, and the like, and fats and fat soluble components, including fatty acids (preferably conjugated), cholesterol, phospholipids and their precursors. Components of a standard serum-free media formulation are listed in Table 1 and include the components found in "DMEM/F-12", available from media manufacturers, such as Grand Island Biological Co. (GIBCO), Grand Island, N.Y. For a review of animal cell culture media, see Mizrahi and Lazar, *Cytotechnology*, 1:99–214 (1988). Media considerations for insect cell cultures are disclosed in Goodwin, R. H. (1990) *Nature* 347:209–210. An exemplary defined serum-free medium individualized for hybridoma cultivation is described by Kovar, J. (1987) *Folia Biologia* 33:377–384. Imagawa et al. (1989) *PNAS* 86:4122–4126 describe individualized media developed to maximize cell growth in mouse mammary epithelial cells, and Miyazaki et al. (1991) *Res. Exp. Med.* 191:77–83 describe media individualized to enhance rat hepatocyte cell viability in vitro.

TABLE 1

| Standard Media Components |
|---|
| Inorganic Salts: |
| $CaCl_2$ (anhyd.) |
| $CuSO_4.5H_2O$ |
| $Fe(NO_3)_3.9H_2O$ |
| $FeSO_4.7H_2O$ |
| KCl |
| $MgCl_2$ |
| $MgSO_4$ |
| NaCl |
| $NaH_2PO_4.H_2O$ |
| $Na_2HPO_4$ |

TABLE 1-continued

| Standard Media Components |
|---|
| $ZnSO_4.7H_2O$ |
| Vitamins |
| Biotin |
| D-Ca pantothenate |
| Choline chloride |
| Folic acid |
| i-Inositol |
| Niacinamide |
| Pyridoxal.HCl |
| Pyridoxine.HCl |
| Riboflavin |
| Thiamine.HCl |
| Thymidine |
| Vitamin $B_{12}$ |
| Other Components: |
| D-Glucose |
| Na hypoxanthine |
| Linoleic acid |
| Lipoic acid |
| Phenol red |
| Putrescine.2HCl |
| Sodium pyruvate |
| Amino acids |

Thus, the invention provides serum-free media with improved cell culture properties, which include standard serum-free medium components as well as an additive, formed, in one embodiment, by the acid or base hydrolysis of a phosphoglyceride ester. The serum-free medium can be purchased from a media manufacturer or created de novo in the laboratory. The proportions of the components of the serum-free medium can be adjusted and optimized for the particular cell line or protein expression system utilized. To enhance the cell cultivation properties of the medium, in addition to the additive, the serum-free medium also may be supplemented with other components, such as a fatty acids, amino acids, or phospholipid precursors.

The medium components typically can be added in any order and the final combination sterilized using a standard methodology, e.g., by filter sterilization.

The serum-free media of the invention may be utilized to improve the cell cultivation properties of a wide range of cells, both vertebrate and invertebrate, as well as the biologicals production properties of these cells. The serum-free media is anticipated to have particular utility in cell culture systems designed for vaccine or recombinant protein production. Thus, the serum-free media of the invention may be used to improve the cell culture properties in many different cell culture systems.

The invention will be understood further from the following nonlimiting examples.

C. Examples

EXAMPLE 1

In this example, the effect of an additive, hydrolyzed phosphatidyl choline, on the cell culture properties of a serum-free medium was examined. The serum-free medium additive was produced by the hydrolysis of a phosphatidyl choline composition purchased from Sigma Co., St. Louis, Mo. The composition is derived from hen egg and its fatty acid chain components are a mixture primarily of palmitic, stearic, linoleic and oleic acids. Solutions of hydrolyzed phosphatidyl choline were generated by both an acid catalyzed hydrolysis and by base saponification. Acid hydrolysis was implemented by dissolving 30 mg phosphatidyl choline in 1 ml ethanol. 100 µl of 1N (1M) HCl then was added, and the solution heated in a water bath at 60° to 70° C. for 30 minutes, to produce the additive (PC(A)). The base saponification was implemented by adding 30 mg of phosphatidyl choline to 1 mL ethanol and 100 µL 1N (1M) NaOH. The solution then was heated to 60°–70° C. in a water bath for 30 minutes, to form the additive (PC(B)).

The effect of the two hydrolyzed solutions on cell growth, cell viability and protein production was examined as follows. CHO-1 cells, chinese hamster ovary cells adapted to express the recombinant osteogenic protein OP-1, were cultured in the presence and absence of either PC(A) or PC(B). The osteogenic protein OP1, is a bone morphogen capable of inducing the cascade of events that result in true tissue regeneration, including endochondral bone formation. Osteogenic protein is described, for example, in U.S. Pat. Nos. 4,968,590, and 5,011,691. Stable OP1 transfectants were created essentially as described in international application PCT/US90/05903 (WO91/05802), published May 2, 1991, the disclosure of which is incorporated herein by reference. Briefly, DNA encoding OP-1 and DHFR were co-transfected into CHO cells and the cells induced to grow in the presence of methotrexate. Stable cell lines were generated for selected gene-amplified clones.

In the experiment, CHO-1 cells were grown in a serum-free medium, "Medium 1", under three different conditions. In a control run, CHO-1 cells were cultured in Medium 1 with a phosphatidyl choline (PC) composition (Sigma Co.) added at a concentration of 30 mg/L. In a second run, CHO-1 cells were grown in Medium 1 in the presence of 1 ml of PC(A) per liter of media. In a third run, CHO-1 cells were cultured in Medium 1 in the presence 1 ml of PC(B) per L of media. "Medium 1" in all cases is a standard media composition, e.g., DMEM/F12, described in Table I and available from GIBCO, transfected for OP1 expression to which, for example, methotrexate has been added.

The results are presented in FIG. 1 where numbers of viable cells/mL is plotted as a function of day of culture. Cell growth in the presence of Medium 1 alone is indicated by solid squares, growth in the presence of Medium 1 plus PC(A) is indicated by open squares; and growth in the presence of Medium 1 plus PC(B) is indicated by solid diamonds. Viable cell density was measured with Trypan blue stain and a hemocytometer. As can be seen in the figure, the addition of hydrolyzed phosphatidyl choline to Medium 1 increased maximum viable cell density 20%, i.e., from a maximum of 900,000 cells/ml, using non-hydrolyzed phosphatidyl choline (PC), to a maximum density of 1,100,000 cells/ml, with medium including either PC(A) or PC(B). Additionally, the slope of the lines in FIG. 1 indicates that CHO-1 cell growth rate was faster in cells provided with PC(A) or PC(B) as compared with the control cells with PC.

EXAMPLE 2

In this example, the effect of acid hydrolyzed phosphatidyl choline, PC(A) in combination with a second, different medium, "Medium 2", was evaluated. Medium 2 is a variant of Medium 1, also adapted for OP-1 expression, e.g., including, for example, methotrexate, as well as the phospholipid precursor ethanolamine, and additional amino acids to double the total amino acid contribution.

Figure 2:
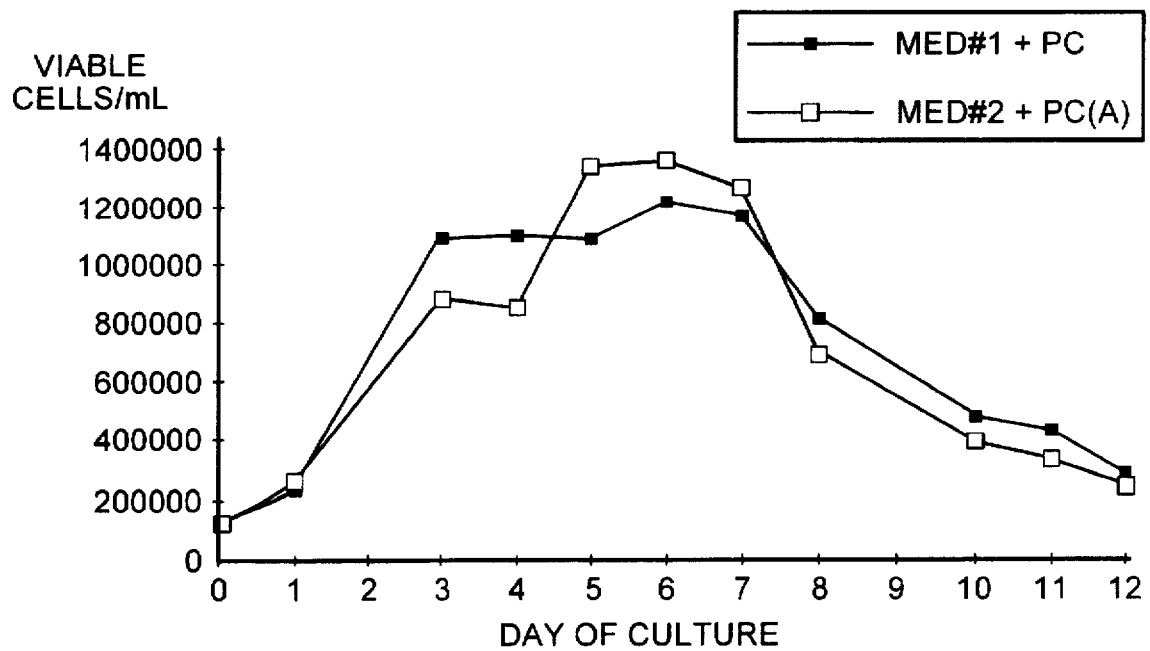
FIG. 2 is a graph of viable cell density versus day of culture for CHO-1 cells.

The cell growth and OP-1 expression of CHO-1 cells in Medium 1 supplemented with PC (30 mg/L) was compared with that of CHO-1 cells in Medium 2 supplemented with PC(A) (30 mg/L) as described in Example 1. The results presented in FIG. 2 demonstrate that the density of viable cells is greater for CHO-1 cells grown in Medium 2 plus PC(A) (open squares) as compared with the density of cells grown in the control medium, e.g., Medium 1 plus non-hydrolyzed phosphatidyl choline (PC, solid squares).

Figure 3:
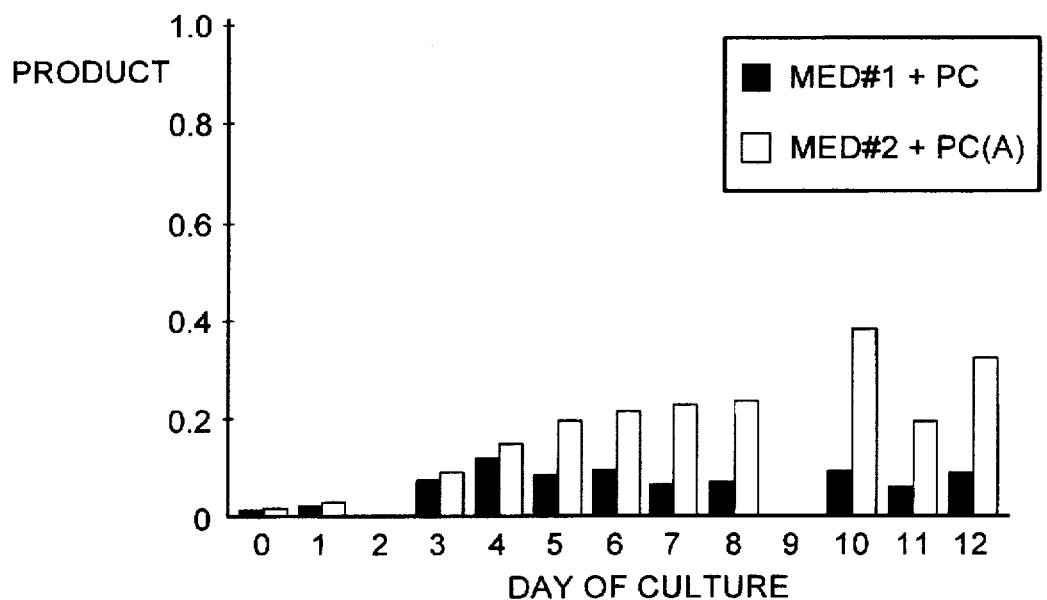
FIG. 3 is a graph of OP-1 production versus day of culture by CHO-1 cells.

Similarly, in FIG. 3, OP-1 production increased 2–3 fold in serum-free Medium 2 plus PC(A) as compared with the control Medium 1. (In the figure, Medium 1 plus PC is represented by a solid bar and Medium 2 plus PC(A) is represented by an open bar.) In a separate control experiment, Medium 2 alone, without the addition of hydrolyzed phosphatidyl choline, was found to have only a marginally beneficial effect on the cell culture properties, as compared with Medium 1 alone. The improved cell culture properties demonstrated in FIGS. 2 and 3, therefore, are due primarily to the presence of the hydrolyzed phosphatidyl choline in the medium.

The addition of hydrolyzed phospholipid to Medium 1 or Medium 2 therefore, synergistically enhances the cell culture properties of the medium.

EXAMPLE 3

In this example, the effect of hydrolyzed phosphatidyl choline, PC(A), on growth and expression of a second cell line, "CHO-2" cells, in serum-free Medium 2 was examined. CHO-2 cells are different, independently created chinese hamster ovary cell line adapted to express the osteogenic protein OP-1 and adapted to grow in methotrexate. Cells were grown in Medium 1 plus non-hydrolyzed phophatidyl choline, PC, (30 mg/L) as a control, and in Medium 2 plus PC(A), 30 mg/L, prepared as for Example 2.

Figure 4:
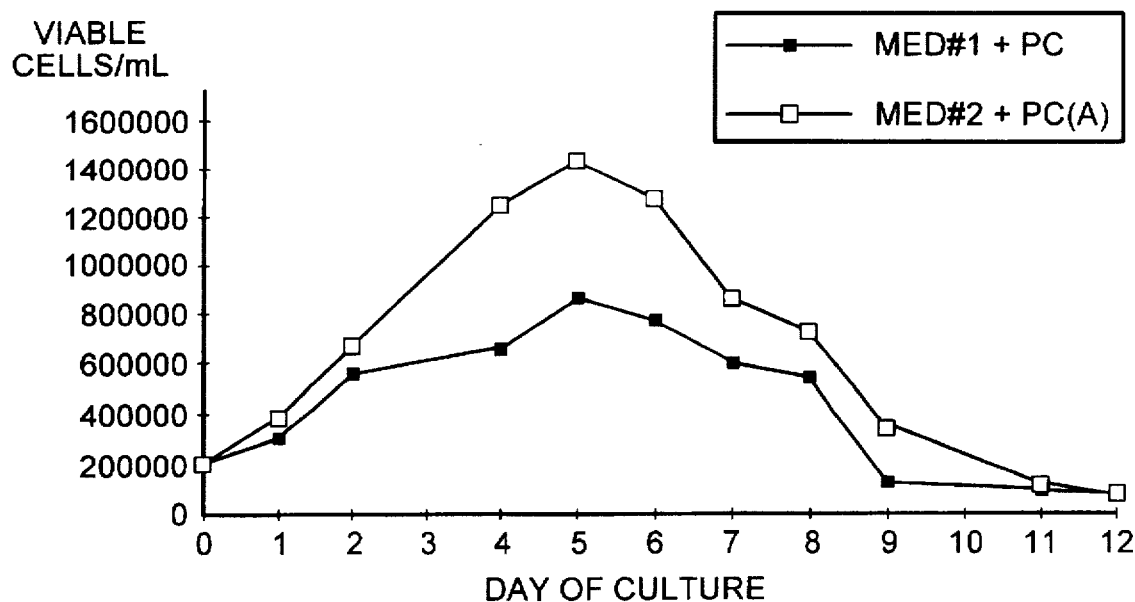
FIG. 4 is a graph of viable cell density versus day of culture for CHO-2 cells.
Figure 5:
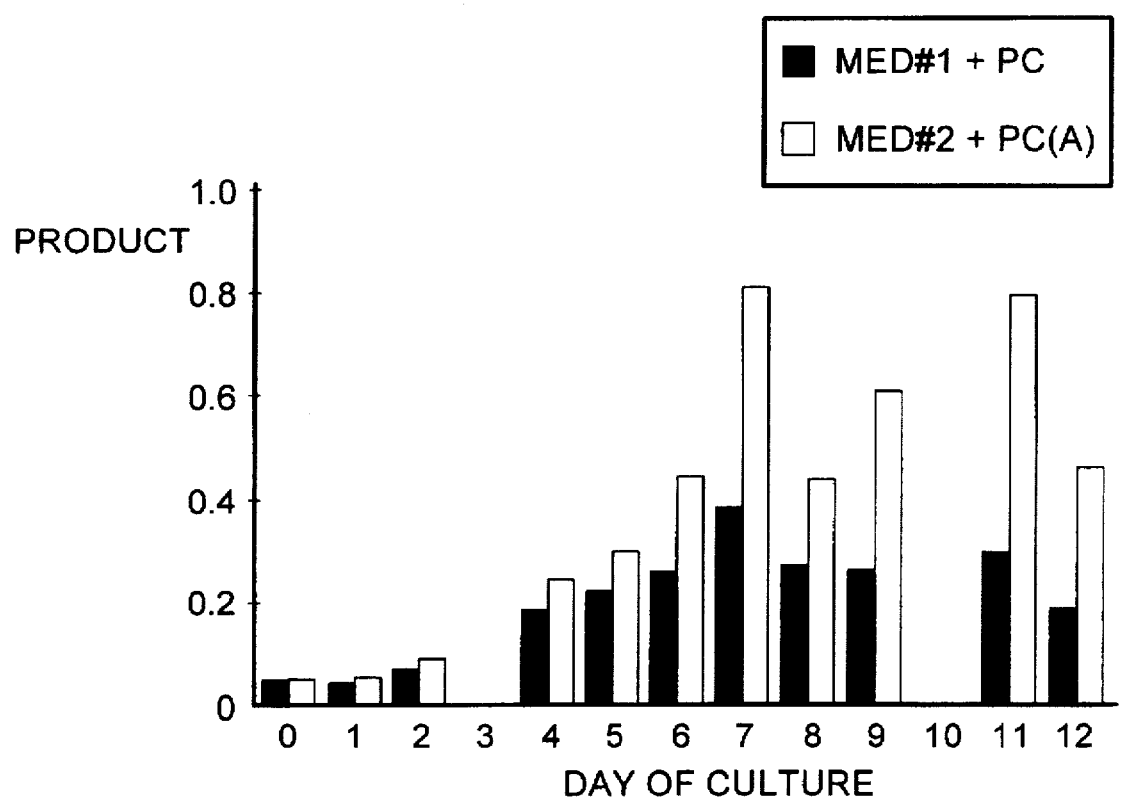
FIG. 5 is a graph of OP-1 production versus day of culture for CHO-2 cells.

As illustrated in FIGS. 4 and 5, both viable cell growth and recombinant protein expression of CHO-2 cells were enhanced in the presence of Medium 2 plus PC(A). FIG. 4 is a graph of viable cell density versus day of culture. As illustrated in FIG. 4, cell growth and cell density of CHO-2 cells is 30–45% greater in Medium 2 plus PC(A) (open squares) as compared with the control medium (solid squares). As illustrated in FIG. 5, OP-1 production was 2–3 times greater in Medium 2 plus PC(A) as compared with the control medium (control is represented by a solid bar, and Medium 2 plus PC(A) is represented by an open bar in the figure.) In a separate control experiment, the enhanced cell culture properties were found to be attributable primarily to the addition of hydrolyzed phosphatidyl choline to the medium, as CHO-2 cells grown in Medium 2, alone, demonstrated only marginally beneficial effects as compared with CHO-2 cells grown in Medium 1 alone.

Thus, the addition of hydrolyzed phospholipid to Medium 2 synergistically enhances the overall cell culture properties of the medium in different cell lines.

EXAMPLE 4

The effect of hydrolyzed phosphatidyl choline PC(A) on the growth of CHO-3 cells, a third chinese hamster ovary cell line, transfected to express a synthetic DNA encoding human insulin growth factor-1, IGF-1, was examined in this example. The cDNA for human IFG-1 is described, for example, in Jansen et al., Nature, 306:609–611 (1983).

In the experiment, CHO-3 cells were grown in a serum-free medium, Medium 3 alone (no hydrolyzed phospholipid, control) or in the presence of hydrolyzed phosphatidyl choline (PC(A), 30 mg/L) and additional amino acids. "Medium 3" is a variant of Medium 1, adapted for IGF-1 expression and including linoleic acid. Cells were grown in suspension at 37 C., and counted on day 4 and day 7 as for Examples 1–3 above, e.g., with a hemocytometer.

The presence of hydrolyzed phosphatidyl choline in the medium was found to greatly improve the cell growth of CHO-3 cells in culture. The viable cell density in the control (Medium 3 alone) was 600,000/ml after 4 days and 740,000/ml after 7 days. By contrast, the viable cell density of CHO-3 cells grown in the same medium supplemented with hydrolyzed phosphatidyl choline increased to 710,000/ml after 4 days and 1,080,000/ml after 7 days, an improvement of 25%.

Thus, the addition of hydrolyzed phospholipid to a medium synergistically enhances the overall cell culture properties of the medium in cell lines adapted to express different biologicals, including different recombinant proteins.

Other Embodiments

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An improved serum-free cell culture medium having improved cell viability or recombinant protein production properties, wherein the improvement comprises an additive formed by alchohol hydrolysis of an intact phosphoglyceride ester defining a substituted glycerol wherein the hydroxyl group at each of C1 and C2 is esterified to the carboxyl group of a fatty acid and the C3 is esterified to a phosphate, the alcohol hydrolysis being sufficient to release one alkylated fatty acid ester from said phosphoglyceride.

2. The medium of claim 1 wherein said alcohol is ethanol.

3. The medium of claim 1 wherein said additive is a reaction product of a base saponification or acid hydrolysis.

4. The medium of claim 3 wherein said base saponification comprises exposing said phosphoglyceride ester to an alcohol solution having pH in the range of about 8—14.

5. The medium of claim 4 wherein said alcohol solution has a pH in the range of 10–14.

6. The medium of claim 4 wherein said alcohol solution comprises a concentration of 0.05M to 10.0M of a base selected from the group consisting of sodium hydroxide, potassium hydroxide and ammonium hydroxide.

7. The medium of claim 3 wherein said acid hydrolysis comprises exposing said phosphoglyceride ester to an alcohol solution having pH in the range of about 0.2–4.

8. The medium of claim 7 wherein said alcohol solution has a pH in the range of 0.2–2.

9. The medium of claim 7 wherein said alcohol solution comprises a concentration of about 0.05M to 10M of an acid selected from the group consisting of hydrochloric acid, sulfuric acid, phosphoric acid and nitric acid.

10. The medium of claim 1 wherein said phosphoglyceride ester is heated to a temperature greater than 40° C.

11. The medium of claim 10 wherein said phosphoglyceride ester is heated to a temperature in the range of about 45°–90° C.

12. The medium of claim 11 wherein said phosphoglyceride ester is heated to a temperature in the range of about 50°–65° C.

13. The medium of claim 10 wherein said phosphoglyceride ester is heated for at least 15 minutes.

14. The medium of claim 1 wherein the phosphoglyceride ester is a cell membrane phospholipid.

15. The medium of claim 1 wherein the phosphoglyceride ester is selected from the group consisting of phosphatidyl serine, phosphatidyl ethanolamine, phosphatidyl choline, and phosphatidyl inositol.

16. The medium of claim 1 further comprising a phospholipid precursor.

17. The medium of claim 16 wherein said precursor comprises ethanolamine.

18. The medium of claim 1 further comprising one or more amino acids.

19. A method of improving a cell cultivation property selected from growth rate, viability or production of a recombinant or naturally-source protein of a mammalian, xenopus or insect cell cultured ex vivo, the method comprising the step of cultivating said cell in the serum free medium of claim 1.

20. The method of claim 19 for improving said cell cultivation property of Chinese hamster ovary cells.

21. The medium of claim 1 wherein the additive comprises the alcohol hydrolyzed phosphoglyceride ester and at least one fatty acid chain released from said phosphoglyceride ester.

22. A method of improving the cell cultivation or biologicals production properties of a serum-free cell culture medium comprising the step of:

adding to a serum-free cell culture medium an additive formed by alcohol hydolysis of an intact phosphoglyceride ester defining a substituted glycerol wherein the hydroxyl group at each of C1 and C2 is esterified to the carboxyl group of a fatty acid and the C3 is esterified to a phosphate, the alcohol hydrolysis being sufficient to release one alkylated fatty acid ester from said phosphoglyceride.

23. The method of claim 22 wherein the phosphoglyceride ester is selected from the group consisting of phosphatidyl choline, phosphatidyl serine, phosphatidyl ethanolamine, and phosphatidyl inositol.

24. The method of claim 22 wherein the medium further comprises a phospholipid precursor.

25. The method of claim 22 wherein said precursor comprises ethanolamine.

26. The method of claim 22 wherein the medium further comprises one or more amino acids.

27. The method of claim 22 wherein the additive comprises the alcohol hydrolysed phosphoglyceride ester and at least one alkylated fatty acid ester released from said intact phosphoglyceride.

* * * * *

UNITED STATES PATENT AND TRADEMARK OFFICE
CERTIFICATE OF CORRECTION

PATENT NO. : 5,631,159
DATED : May 20, 1997
INVENTOR(S) : Paul G. Marshall and Patrick M. Guertin It is certified that error appears in the above-indentified patent and that said Letters Patent is hereby corrected as shown below:

Col. 11, claim 1, line 31, change "alchohol" to -- alcohol --.

Col. 12, claim 25, line 50, change "22" to -- 24 --.

Signed and Sealed this

Second Day of September, 1997

Attest:

BRUCE LEHMAN

Attesting Officer

Commissioner of Patents and Trademarks